(12) United States Patent
Zhang et al.

(10) Patent No.: US 11,635,399 B2
(45) Date of Patent: Apr. 25, 2023

(54) INSTRUMENT FOR MASTITIS DETECTION AND ANALYSIS

(71) Applicant: APTACAM HONG KONG LIMITED, Hong Kong (CN)

(72) Inventors: Yang Zhang, Hong Kong (CN); Lei Fang, Hong Kong (CN)

(73) Assignee: APTACAM HONG KONG LIMITED, Hong Kong (CN)

( * ) Notice: Subject to any disclaimer, the term of this patent is extended or adjusted under 35 U.S.C. 154(b) by 152 days.

(21) Appl. No.: 16/928,018

(22) Filed: Jul. 14, 2020

(65) Prior Publication Data
US 2021/0278356 A1 Sep. 9, 2021

(30) Foreign Application Priority Data
Mar. 5, 2020 (CN) .......................... 202010146674.8

(51) Int. Cl.
*G01N 27/07* (2006.01)
*G01N 33/487* (2006.01)
*G01K 13/00* (2021.01)

(52) U.S. Cl.
CPC ............. *G01N 27/07* (2013.01); *G01K 13/00* (2013.01); *G01N 33/487* (2013.01)

(58) Field of Classification Search
CPC ...... G01N 27/07; G01N 33/487; G01N 27/06; G01N 33/04; G01K 13/00; G01K 13/02; G01K 13/026; A01J 5/0133; A01J 5/0138
See application file for complete search history.

(56) References Cited

U.S. PATENT DOCUMENTS

| | | | | |
|---|---|---|---|---|
| 4,385,590 A | * | 5/1983 | Mortensen | A01J 7/00 119/14.01 |
| 2007/0202160 A1 | * | 8/2007 | Hageman | A61P 43/00 424/452 |
| 2019/0174950 A1 | * | 6/2019 | Hendrickson | A47J 31/402 |
| 2019/0254249 A1 | * | 8/2019 | Caamaño | A01K 29/00 |
| 2019/0307099 A1 | * | 10/2019 | Mostert | A01J 5/08 |
| 2021/0360891 A1 | * | 11/2021 | Suhr | A01J 5/0133 |

* cited by examiner

*Primary Examiner* — Christopher P McAndrew
*Assistant Examiner* — Zannatul Ferdous

(57) ABSTRACT

The present patent application provides an instrument for mastitis detection and analysis, comprising: a computing module, a conductivity detection module and a temperature sensor; the conductivity detection module is used to detect the conductivity of a sample, and is used to send the detected sample conductivity data to the computing module; the temperature sensor is used to detect the sample temperature, and is used to send the sample temperature data to the computing module; the computing module is used to calculate the received sample conductivity and the sample temperature through a detection algorithm, and is used to detect and analyze the mastitis of the sample through the detection algorithm. The instrument for mastitis detection and analysis is convenient to be carried and easy-to-use, it can be quickly immerged into a milk sample to complete the detection, and the detection result can be obtained quickly.

9 Claims, 3 Drawing Sheets

INSTRUMENT FOR MASTITIS DETECTION AND ANALYSIS

TECHNICAL FIELD

The application relates to the field of mastitis detection technology; and in particular to an instrument for mastitis detection and analysis.

BACKGROUND

Mastitis, also known as mammary abscess, milk yellow, and mammary tumidness; it is caused by blood stasis and poisonous gas coagulating on breast and becoming carbuncle swelling, breasts appear stiff, swollen, hot and painful; it is more common in postpartum lactating animals, especially in cows which are in lactating period; in livestock, it is more common in cows and dairy goats; it also occurs in horses and sheep. Take cows as an example; mastitis causes huge economic losses to the dairy industry worldwide, it reduces the yield and quality of dairy products, and economic losses due to mastitis exceed 10 billion dollars per year. The key to controlling this disease is to achieve rapid and accurate detection, so that effective prevention and cure can be given on time.

Nowadays, three mainstream detection instruments on the market are somatic cell number detector, California mastitis test device and conductivity detector. However, none of these detection instruments can fully meet the detection needs of the dairy enterprises and farmers. The somatic cell number detector needs to detect somatic cells in the laboratory and it takes significant time for detection, which delays the detection and treatment of mastitis. The California mastitis test device needs to complete a mini experiment in about six minutes, which is time-consuming and inconvenient. The conductivity detector is easily affected by many environmental factors, which leads to detection errors. Therefore, how to solve the problem of mastitis detection instrument has important practical value. Meanwhile, considering that users are mostly culture farmers, it is necessary to design a simple and easy-to-use detection instrument.

SUMMARY

The present patent application provides an instrument for mastitis detection and analysis, the detection result can be obtained quickly by using the instrument for mastitis detection and analysis, the instrument for mastitis detection and analysis is convenient to be carried and easy-to-use, the detection result can be obtained quickly.

The present patent application provides an instrument for mastitis detection and analysis, and the instrument for mastitis detection and analysis comprises a computing module, a conductivity detection module and a temperature sensor; the computing module is respectively connected to the conductivity detection module and the temperature sensor; the conductivity detection module is used to detect the conductivity of a sample, and is used to send the detected sample conductivity to the computing module; the temperature sensor is used to detect the temperature of a sample, to obtain a sample temperature, and is used to send the sample temperature to the computing module; the computing module is used to calculate the received sample conductivity and the sample temperature through a detection algorithm, and is used to detect and analyze the mastitis of the sample through the detection algorithm.

Preferably, the conductivity detection module comprises a conductivity detection probe, the conductivity detection probe is used to detect the sample conductivity.

Preferably, the conductivity detection module further comprises an amplifier, the amplifier is connected to the computing module; the conductivity detection probe is connected to the amplifier; the amplifier is used to perform signal amplification of the sample conductivity which is detected by the conductivity detection probe and then transmit the signal to the computing module.

Preferably, the conductivity detection probe comprises a fluid guiding device, the fluid guiding device is connected to the end of the detection probe for diversion of the sample.

Preferably, the fluid guiding device is made by food-grade stainless steel material.

Preferably, the conductivity detection probe is directly immerged into the sample for detection.

Preferably, the detection algorithm ran by the computing module comprises:

when satisfying: $E_i - aT_i \leq b$, the mastitis detection result shows animal is healthy;

when satisfying: $aT_i + b < E_i < cT_i + d$, the mastitis detection result suggests animal with suspected infection;

when satisfying: $E_i - cT_i \geq d$, the mastitis detection result suggests animal with infection;

where $T_i$ is the sample temperature, $E_i$ is the sample conductivity, a and c are slopes, h and d are intercepts; the slopes and the intercepts are obtained by detecting the conductivity of a certain number of normal and abnormal samples under different temperature conditions, and then through linear fitting to establish the equations of the sample conductivity at different temperatures for calculating; a and b are the slopes and the intercepts of the conductivity fitting equation for normal samples, respectively; c and d are the slopes and the intercepts of the conductivity fitting equation for abnormal samples, respectively; specifically, calibrating the sample conductivity under different temperatures can eliminate testing error and achieve accurate detection.

Preferably, the slopes and the intercepts are calculated from measuring a certain number of samples, which are based on regions and animal species.

Preferably, the instrument for mastitis detection and analysis is handheld instrument.

Preferably, the instrument for mastitis detection and analysis further comprises:

a display device, which is provided on the surface of the instrument for mastitis detection and analysis and is used to provide a visualized result display;

a power module, which is used to provide a power input for the instrument for mastitis detection and analysis;

an on-off key, which is provided on the surface of the instrument for mastitis detection and analysis and is used to turn on or turn off the instrument for mastitis detection and analysis.

Compared to the prior art, the instrument for mastitis detection and analysis provided by the present patent application detects the sample conductivity and sample temperature, the instrument for mastitis detection and analysis can obtain mastitis detection result rapidly and accurately. The instrument for mastitis detection and analysis is convenient to be carried and easy-to-use, it can be quickly immerged into a milk sample to complete the detection, and the detection result can be obtained quickly.

BRIEF DESCRIPTION OF THE DRAWINGS

In order to illustrate the technical solution relating in the embodiment of the present patent application more clearly, the drawings used in the description of the embodiments are briefly introduced below. Obviously, the drawings in the following description are only some embodiments of the present patent application, for those of ordinary skill in the art, other drawings can be obtained based on these drawings without any creative work, where.

DESCRIPTION OF EMBODIMENTS

The technical solution relating in the embodiments of the present patent application will be clearly and completely described below with reference to the drawings in the embodiments of the present patent application, obviously, the described embodiments are only a part of the embodiments of the present patent application, but not all the embodiments. Based on the embodiments of the present patent application, all other embodiments obtained by a person of ordinary skill in the art without creative efforts shall fall within the protection scope of the present invention.

Figure 1:
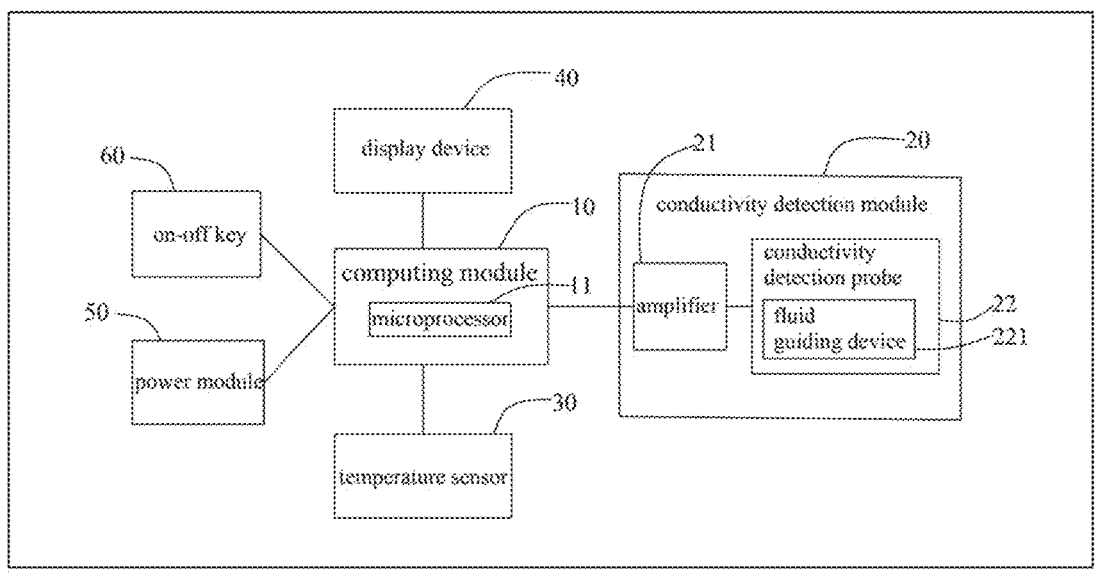
FIG. 1 is a structure schematic diagram of an instrument for mastitis detection and analysis provided by an embodiment of the present patent application.

Please refer to FIG. 1, the present patent application provides an instrument for mastitis detection and analysis, which comprises a computing module 10, a conductivity detection module 20, a temperature sensor 30, a display device 40, a power module 50, and an on-off key 60; the computing module 10 is respectively connected to the conductivity detection module 20 and the temperature sensor 30; the display device 40 is provided on the surface of the instrument for mastitis detection and analysis and is used to provide a visualized result display; the power module 50 is provided inside the instrument for mastitis detection and analysis to provide a power to the instrument for mastitis detection and analysis, the power comprises an external power and a built-in battery power; the on-off key 60 is provided on the surface of the instrument for mastitis detection and analysis and is used to turn on or turn off the instrument for mastitis detection and analysis.

The conductivity detection module 20 is used to detect the conductivity of a sample, and is used to send the detected sample conductivity to the computing module 10; specifically, the conductivity detection module 20 comprises a conductivity detection probe 22 and an amplifier 21, the amplifier 21 is connected to the computing module 10, the conductivity detection probe 22 is connected to the amplifier 21, the conductivity detection probe 22 is used to detect the sample conductivity, and the signal of the detected sample conductivity data is amplified by the amplifier 21 and transmitted to the computing module 10; the conductivity detection probe 22 comprises a fluid guiding device 221, the fluid guiding device 221 is connected on the end of the detection probe for diversion of the sample; the fluid guiding device 221 prevents the interference of air bubbles or foam during the sample detection process, thereby improving the detection accuracy. Specifically, in one embodiment, the fluid guiding device 221 is food-grade stainless steel material.

The temperature sensor 30 is used to detect the temperature of a sample to obtain a sample temperature, and is used to send the sample temperature to the computing module 10; specifically, the temperature sensor 30 is connected to the conductivity detection probe 22 to test the sample temperature, and the temperature sensor 30 is further connected to the computing module 10 to send the sample temperature data to the computing module 10.

The computing module 10 is used to calculate the received sample conductivity and the sample temperature through a detection algorithm, and is used to detect and analyze the mastitis of the sample through the detection algorithm. Specifically, in one embodiment, the computing module 10 comprises a microprocessor 11, and the microprocessor 11 specifically performs the calculation of the detection algorithm.

The detection algorithm ran by the computing module 10 of the instrument for mastitis detection and analysis is:

when satisfying: $E_i - aT_i \leq b$, the mastitis detection result shows animal is healthy;

when satisfying: $aT_i + b < E_i < cT_i + d$, the mastitis detection result suggests animal with suspected infection;

when satisfying: $E_i - cT_i \geq d$, the mastitis detection result suggests animal with infection;

where $T_i$ is the sample temperature $E_i$ is the sample conductivity, a and c are slopes, b and d are intercepts; the slopes and the intercepts are obtained by detecting the conductivity of a certain number of normal and abnormal samples under different temperature conditions, and then through linear fitting to establish the equations of the sample conductivity at different temperatures for calculating; a and b are the slopes and the intercepts of the conductivity fitting equation for normal samples, respectively; c and d are the slopes and the intercepts of the conductivity fitting equation for abnormal samples, respectively; specifically, calibrating the sample conductivity under different temperatures can eliminate testing error and achieve accurate detection.

When running the detection algorithm, the slopes and the intercepts need to be set, the slopes and the intercepts are calculated from measuring a certain number of samples, which are based on the regions and the animal species.

Specifically, in an embodiment, to detect Holstein cows, corresponding detection algorithm is:

When satisfying: $E_i - 98.806 T_i \leq 2179$ the mastitis detection result suggests animal is healthy;

When satisfying: $98.806 T_i + 2179 < E_i < 123.67 T_i + 2727.3$, the mastitis detection result suggests animal with suspected infection;

When satisfying: $E_i - 123.67 T_i \geq 2727.3$, the mastitis detection result suggests animal with infection.

Here, for Holstein cows in South China, the slope a=98.806, c=123.67; the intercept b=2179, d=2727.3. The slope and the intercept are obtained by measuring the conductivity of milk sample of 6 groups of normal and abnormal Holstein dairy cows under 13 different temperature conditions respectively, and by linear fitting to establish the equations of the sample conductivity under different temperatures for calculating. Specifically, the errors in sample conductivities are calibrated by measuring different temperatures to achieve accurate detection. For different breeds of cows or other animals, for cows in different regions or other animals, the parameters will differ in the linear equation, by using a certain amount of normal samples and infected samples to perform linear calculations separately on the cows of the same breed and the same region, can obtain the slope and the intercept for the cows of the same breed and region, in this way, by setting the slope and intercept in advance, can accurately achieve the mastitis detection calculation for cows of different breeds and regions.

Specifically; the detection data of Holstein cows which provided by an embodiment of the present patent application is shown in Table 1:

instrument for mastitis detection and analysis. There are three detection status in FIG. 3: healthy, suspicious, and infected, when the detection sample is from suspicious cows or cows with subclinical mastitis, the display device 40 shows yellow; when the detection sample is from infected cows, the display device 40 shows red. The test results are

TABLE 1

| Temperature | Normal Milk (Conductivity) | Milk from cows with subclinical mastitis (Conductivity) | Milk from cows with clinical mastitis (Conductivity) | | | |
|---|---|---|---|---|---|---|
| | | | Grade 1 | Grade 2 | Grade 3 | Grade 4 |
| 9 | 3594.29 | 3594-3812 | 3812.56 | 4332.10 | 4870.594 | 5380.984 |
| 10 | 3823.21 | 3823-4055 | 4055.38 | 4608.02 | 5180.802 | 5723.7 |
| 20 | 4820.31 | 4820-5113 | 5113.04 | 5809.79 | 6531.968 | 7216.455 |
| 23 | 5261.63 | 5261-5581 | 5581.16 | 6341.71 | 7129.999 | 7877.153 |
| 24 | 5330.07 | 5330-5653 | 5653.76 | 6424.19 | 7222.742 | 7979.615 |
| 5 | 5499.99 | 5500-5834 | 5834 | 6629 | 7453 | 8234.001 |
| 26 | 5602.65 | 5602-5942 | 5942.89 | 6752.73 | 7592.114 | 8387.693 |
| 27 | 5849.27 | 5849-6204 | 6204.49 | 7049.97 | 7926.307 | 8756.907 |
| 33 | 6276.44 | 6276-6657 | 6657.59 | 7564.82 | 8505.15 | 9396.407 |
| 34 | 6341.34 | 6341-6726 | 6726.43 | 7643.05 | 8593.096 | 9493.569 |
| 36 | 6884.14 | 6884-7302 | 7302.2 | 8297.27 | 9328.642 | 10306.19 |
| 37.5 | 7004.50 | 7004-7429 | 7429.87 | 8442.34 | 9491.741 | 10486.38 |
| 40 | 7303.05 | 7303-7746 | 7746.54 | 8802.16 | 9896.291 | 10933.33 |

Specifically; in Table 1; the unit of temperature is degree centigrade, and the unit of the conductivity is micro-Siemens/cm, which is recorded as μS/cm. For example, when the temperature of the sample is 24 degrees, the conductivity of the normal milk is less than 5330.07 μS/cm; when the conductivity is between 5330 μS/cm and 5653 μS/cm, the cow is with subclinical mastitis or suspected infection; when the conductivity is greater than or equal to 5653.76 μS/cm, the cow is with clinical mastitis or infection. For infected cows, different grade of infection can be further subdivided, specifically in this embodiment, when the conductivity is greater than or equal to 5653.76 μS/cm, it is the first grade of infection; when the conductivity is greater than or equal to 6424.19 μS/cm, it is the second grade of infection; when the conductivity is greater than or equal to 7222.742 μS/cm, it is the third grade of infection; when the conductivity is greater than or equal to 7979.615 μS/cm, it is the fourth grade of infection.

Figure 2:
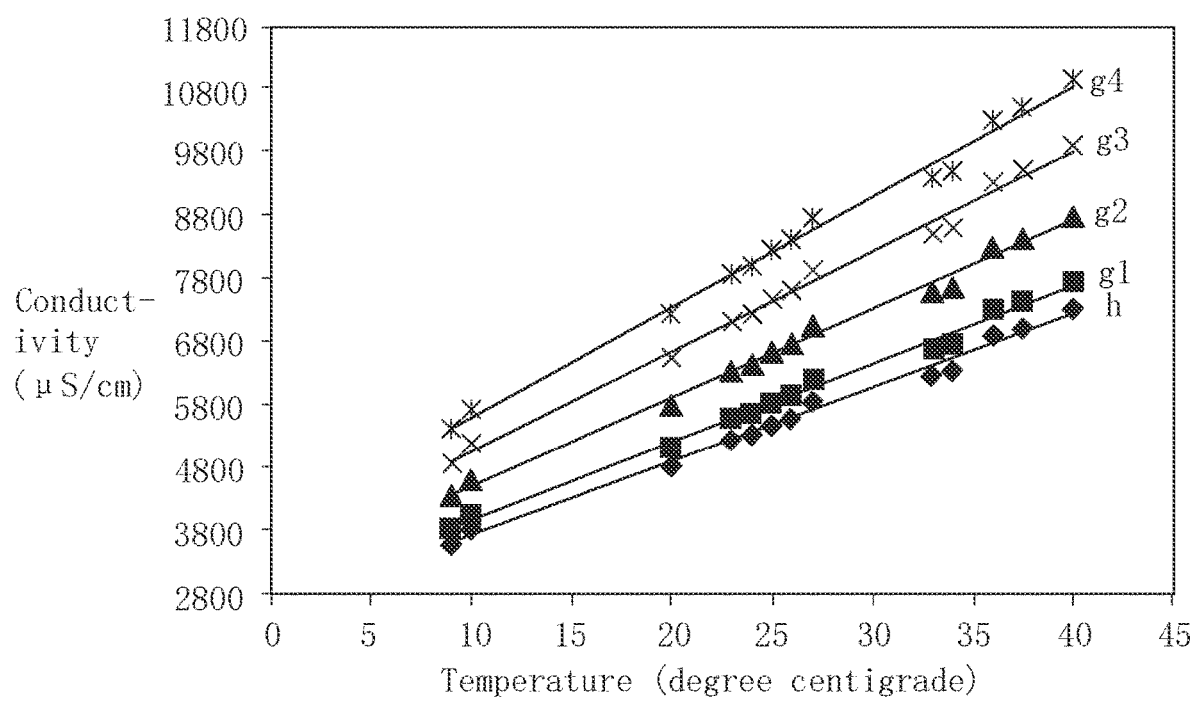
FIG. 2 is a schematic diagram of sample test results of an instrument for mastitis detection and analysis provided by an embodiment of the present patent application.

Please refer to FIG. 2, the test results for different temperatures are shown in FIG. 2, curve h is the test result of normal milk, curve g1 is the test result of the first grade of infection, curve g2 is the test result of the second grade of infection, curve g3 is the test result of the third grade of infection, curve g4 is the test result of the fourth grade of infection.

Figure 3:
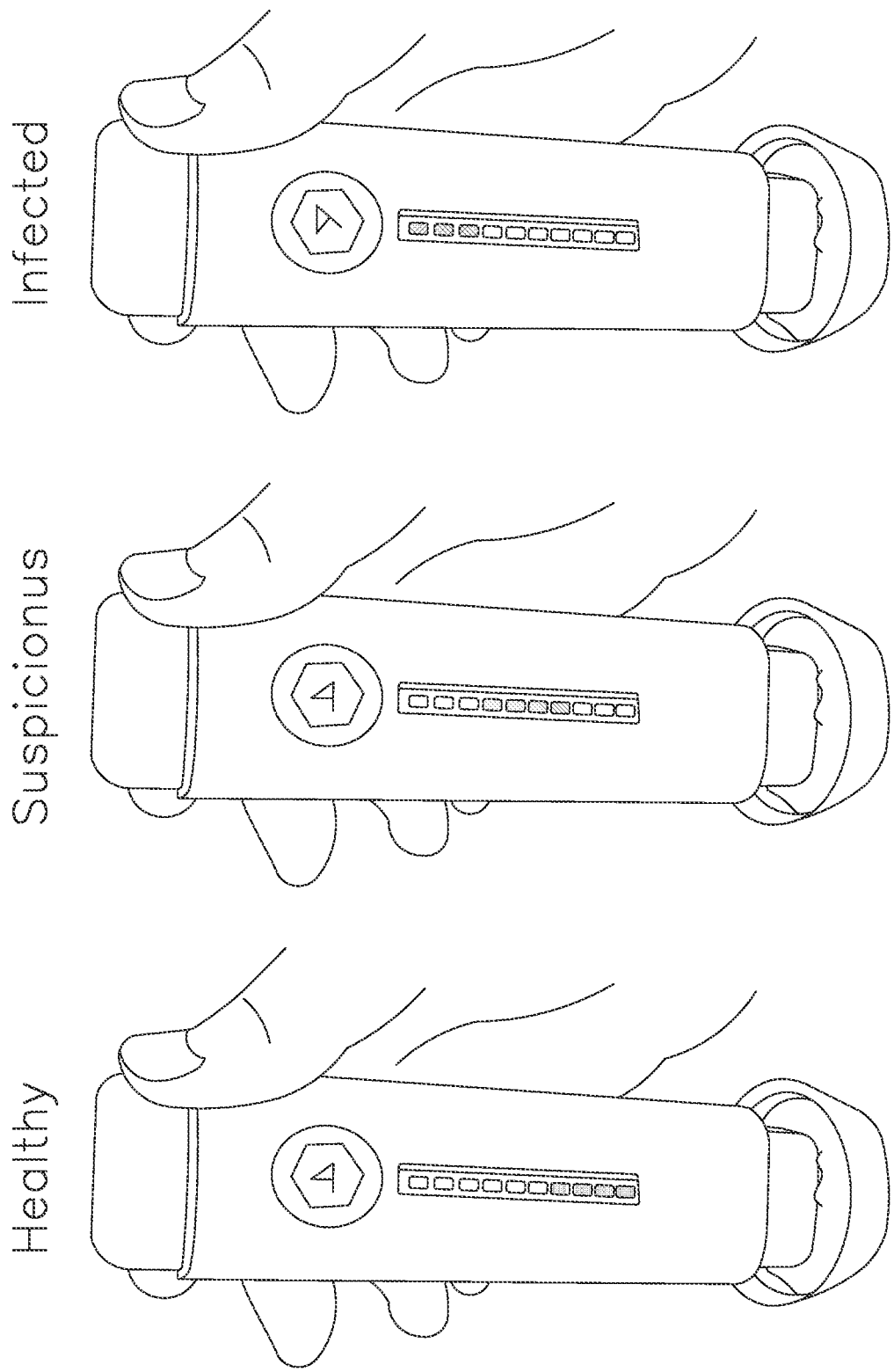
FIG. 3 is a test schematic diagram of an instrument for mastitis detection and analysis provided by an embodiment of the present patent application.

Please refer to FIG. 3, it is a test schematic diagram of the instrument for mastitis detection and analysis, which provided by the embodiment of the present patent application. The instrument for mastitis detection and analysis is handheld, and has a length of 15 centimeters, in other embodiments, the length of the instrument for mastitis detection and analysis is between 10 centimeters and 25 centimeters. The instrument for mastitis detection and analysis may also be of other shapes or implanted in other detection instruments, which all belong to the protection scope of this patent. When testing, insert the conductivity detection probe directly into the milk sample for testing, turn on the on-off key on the outer surface of the instrument for mastitis detection and analysis and the test can be completed in 3 seconds, the test result are displayed directly on the display device 40 of the directly displayed through different colors, which make the instrument for mastitis detection and analysis simple, convenient and easy-to-use, and meet the needs of the majority of farmer users.

Compared to the prior art, the instrument for mastitis detection and analysis provided by the present application detect the sample conductivity and sample temperature, obtaining mastitis detection result rapidly and accurately. The instrument for mastitis detection and analysis is convenient to be carried around and easy-to-use, it can be quickly immerged into a milk sample to complete the detection, and the detection result can be obtained quickly. The instrument for mastitis detection and analysis can be widely used in mammalian mastitis detection, for example, it can be used in cows, dairy goats, horses, sheep, et cetera. For animals of different regions and species, the detector needs to use a certain amount of normal and infected samples from animals to perform linear calculations separately, the samples are animal milk, such as cow milk, goat milk, horse milk, etc., so that, the slopes and intercepts of the animals of the same breed and the same region can be obtained, in this way, by setting the slope and intercept in advance, can accurately achieve the mastitis detection calculation for cows of different breeds and regions.

Note that the above are only the preferred embodiments of the present patent application and the applied technical principles. Those skilled in the art will understand that the present patent application is not limited to the specific embodiments described herein, it will be apparent to those skilled in the art that various obvious changes, readjustments and substitutions can be made without departing from the protection scope of the present patent application. Therefore, although the present patent application has been described in details through the above embodiments, however, the present patent application is not limited to the above embodiments, without departing from the concept of the present patent application, many other equivalent embodiments can be included, and the scope of the present patent application is determined by the scope of the claims.

What is claimed is:

1. An instrument for mastitis detection and analysis, comprising: a computing module, a conductivity detection module and a temperature sensor; the computing module is respectively connected to the conductivity detection module and the temperature sensor; the conductivity, detection module is used to detect the conductivity of a sample; and is used to send the detected sample conductivity to the computing module; the temperature sensor is used to detect the temperature of a sample to obtain a sample temperature, and is used to send the sample temperature to the computing module; the computing module is used to calculate the received sample conductivity and the sample temperature through a detection algorithm, and is used to detect and analyze the mastitis of the sample through the detection algorithm; wherein the detection algorithm ran by the computing module comprises:

when satisfying: $E_i - aT_i \leq b$, the mastitis detection result shows animal is healthy; when satisfying: $aT_i + b < E_i < cT_i + d$, the mastitis detection result suggests animal with suspected infection; and when satisfying: $E_i - cT_i \geq d$, the mastitis detection result suggests animal with infection;

wherein $T_i$ is the sample temperature, $E_i$ is the sample conductivity, a and c are slopes, b and d are intercepts; the slopes and the intercepts are obtained by detecting the conductivity of a certain number of normal and abnormal samples under different temperature conditions; and then through linear fitting to establish the equations of the sample conductivity at different temperatures for calculating; a and b are the slopes and the intercepts of the conductivity fitting equation for normal samples, respectively; c and d are the slopes and the intercepts of the conductivity fitting equation for abnormal samples, respectively; specifically, calibrating the sample conductivity under different temperatures can eliminate testing error and achieve accurate detection.

2. The instrument for mastitis detection and analysis according to claim 1, wherein the conductivity detection module comprises a conductivity detection probe, the conductivity detection probe is used to detect the conductivity of a sample.

3. The instrument for mastitis detection and analysis according to claim 2, wherein the conductivity detection module further comprises an amplifier; the amplifier is connected to the computing module: the conductivity detection probe is connected to the amplifier; the amplifier is used to perform signal amplification of the sample conductivity which is detected by the conductivity detection probe and then transmit the signal to the computing module.

4. The instalment for mastitis detection and analysis according to claim 2, wherein the conductivity detection probe comprises a fluid guiding device; the fluid guiding device is connected to the end of the detection probe for diversion of the sample.

5. The instrument for mastitis detection and analysis according to claim 4, wherein the fluid guiding device is made by food-grade stainless steel material.

6. The instalment for mastitis detection and analysis according to claim 2, wherein the conductivity detection probe is directly immerged into the sample for detection.

7. The instrument for mastitis detection and analysis according to claim 1, wherein the slopes and the intercepts are calculated from the measuring a certain number of samples, which are based on regions and animal species.

8. The instrument for mastitis detection and analysis according to claim 1, wherein the instrument for mastitis detection and analysis is handheld instrument.

9. The instrument for mastitis detection and analysis according to claim 1, wherein the instrument for mastitis detection and analysis further comprises:

a display device, which is provided on the surface of the instrument for mastitis detection and analysis and is used to provide a visualized result display;

a power module, which is used to provide a power input for the instrument for mastitis detection and analysis; and an on-off key; which is provided on the surface of the instrument for mastitis detection and analysis and is used to turn on or turn off the instrument for mastitis detection and analysis.

* * * * *